United States Patent [19]
Longley et al.

[11] Patent Number: 6,087,363
[45] Date of Patent: Jul. 11, 2000

[54] USE OF IMIDAZOLE AND INDOLE COMPOUNDS AS INHIBITORS OF NITRIC OXIDE SYNTHASE

[75] Inventors: Ross E. Longley, Vero Beach; Richard A. Isbrucker; Amy E. Wright, both of Fort Pierce, all of Fla.

[73] Assignee: Harbor Branch Oceanographic Institution, Inc., Ft. Pierce, Fla.

[21] Appl. No.: 09/356,171

[22] Filed: Jul. 16, 1999

Related U.S. Application Data

[60] Provisional application No. 60/093,283, Jul. 17, 1998.

[51] Int. Cl.$^7$ ................................................. A61K 31/495
[52] U.S. Cl. ............................................................ 514/254
[58] Field of Search ............................................ 514/254

[56] References Cited

U.S. PATENT DOCUMENTS

| | | | |
|---|---|---|---|
| 4,866,084 | 9/1989 | Gunasekera et al. | 514/397 |
| 4,895,844 | 1/1990 | Komoto et al. | 514/254 |
| 4,970,226 | 11/1990 | Sun et al. | 514/397 |
| 5,290,777 | 3/1994 | McConnell et al. | 514/254 |
| 5,464,835 | 11/1995 | McConnell et al. | 514/254 |

OTHER PUBLICATIONS

Armin, Ashok, R., Mukundan Attur, Steven B. Abramson (1999) "Nitric oxide synthase and cyclooxygenases: distribution, regulation, and intervention in arthritis" *Current Opinion in Rheumatology* 11(3):202–209.

Baraldi, Eugenio, Cinzia Dario, Riccardo Ongaro, Massimo Scollo et al. (1999) "Exhaled Nitric Oxide Concentrations During Treatment of Wheezing Exacerbation in Infants and Young Children" *Am. J. Respir. Crit. Care Med.* 159(4 Pt. 1):1284–1288.

Bredt, David S., Solomon H. Snyder (1990) "Isolation of nitric oxide synthetase, a calmodulin–requiring enzyme" *Proc. Natl. Ac. Sci. USA* 87:682–685.

Faulkner, D. (1995) *J. Nat. Prod. Rep.* 12–223–269.
Faulkner, D. (1994) *J. Nat. Prod. Rep.* 11:355–394.
Faulkner, D. (1993) *J. Nat. Prod. Rep.* 10:497–539.
Faulkner, D. (1992) *J. Nat. Prod. Rep.* 9:323–364.
Faulkner, D. (1991) *J. Nat. Prod. Rep.* 8:97–147.
Faulkner, D. (1990) *J. Nat. Prod. Rep.* 7:269–309.
Faulkner, D. (1988) *J. Nat. Prod. Rep.* 5:613–663.
Faulkner, D. (1987) *J. Nat. Prod. Rep.* 4:539–576.
Faulkner, D. (1986) *J. Nat. Prod. Rep.* 3:1–33.
Faulkner, D. (1984) *J. Nat. Prod. Rep.* 1:551–598.

Fukuto, J.M. and G. Chaudhuri (1995) "Inhibition Of Constitutive And Inducible Nitric Oxide Synthase: Potential Selective Inhibition" *Annu. Rev. Pharmacol. Toxicol.* 35:165–194.

Gahtan, Ethan, J. Bruce Overmier (1999) "Inflammatory pathogenesis in Alzheimer's disease: biological mechanisms and cognitive sequeli" *Neurosciences and Biobehavioral Reviews* 23:615–633.

Greenberg, Stan S., Jianming Xie, John J. Spitzer et al. (1995) "Nitro Containing L–Arginine Analogs Interfere With Assays For Nitrate And Nitrite" *Life Sciences* 57(21):1949–1961.

Gunasekera, Sarath P., Peter J. McCarthy, Michelle Kelly–Borges (1994 Hamacanthins A and B, New Antifungal Bis Indole Alkaloids From The Deep–Water Marine Sponge, *Hamacantha Sp.* 57(10):1437–1441.

Handy, Rachael L.C., H.L. Harb, P. Wallace, Z. Gaffen, K.J. Whitehead, P.K. Moore (1996) "Inhibition of nitric oxide synthase by 1–(2–trifluoromethylphenyl) imidazole (TRIM) in vitro: antinociceptive and Cardiovascular effects" *British J. of Pharmacology*119:423–431.

Hays, Sheryl J. (1998) "Therapeutic Approaches to the Treatment of Neuroinflammatory Diseases" *Current Pharmaceutical Design* 4:335–348.

Klee, Claude B., Hao Ren, Xutong Wang (1998) "Regulation of the Calmodulin–stimulated Protein Phosphatase, Calcineurin" *J. Biological Chemistry* 273(22):13367–13370.

Kohmoto, Shigeo, Yoel Kashman, Oliver J. McConnel, Kenneth L. Rinehart, Jr., Amy Wright, Frank Koehn (1988) "Dragmacidin, a New Cytotoxic Bis(indole) Alkaloid from a Deep Water Marine Sponge, Dragmacidon sp." *J. Organic Chemistry* 53:3116–3118.

McCann, S.M. (1997) "The Nitric Oxide Hypothesis Of Brain Agin" *Experimental Gerontology* 32(4/5):431–440.

McCann, S.M., J. Licinio, M.L. Wong et al. (1998) "The Nitric Oxide Hypothesis Of Aging" *Experimental Gerontology* 33(7/8):813–826.

Molina et al. (1998) "The Role of Nitric Oxide in Neurodgeneration" *Drugs & Aging* 12(4):251–259.

Mosmann, Tim (1983) "Rapid Colorimetric Assay for Cellular Growth and Survival: Application to Proliferation and Cytotoxicity Assays" *J. Immunol. Methods* 65:55–63.

Moquin, Carole, Michele Guyot (1984) *Tetrahedron Letters* 25(44):5047–5048.

Norton, Raymond S., Robert J. Wells (1982) "A Series of Chiral Polybrominated Biindoles from the Marine Blue–Green Alga Rivularia firma. Application . . . Elucidation" J. Am. Chem. Soc. 104:3628–3635.

Ohshima, H., S. Oguchi, H. Adachi, S. Iida, H. susuki, T. Sugimura, H. Esumi (1992) "Purification of Nitric Oxide Synthase from Bovine Brain: Immunological Characterization and Tissue Distribution" *Biochemical and Biophysical Research Communications* 183(1):238–244.

(List continued on next page.)

*Primary Examiner*—Raymond Henley, III
*Attorney, Agent, or Firm*—Saliwanchik, Lloyd & Saliwanchik

[57] ABSTRACT

Imidazole and indole compounds were found to inhibit neural nitric oxide synthase (bNOS) activity. Nortopsentin-C inhibited bNOS as well as calcineurin activities suggesting that its actions are directed against calmodulin, a co-factor common to these two enzymes. Two indole compounds, as well as dragmacidin-D, inhibited bNOS, but not calcineurin, activity. Murine macrophage viability and induced NOS (iNOS) activity in cultured cells was also unaffected by these compounds.

7 Claims, 3 Drawing Sheets

OTHER PUBLICATIONS

Sakemi, Shinichi, Hao H. Sun (1991) "Nortopsentins A, B, and C. Cytotoxic and Antifungal Imidazolediylbis[indoles] from the Sponge *Spongosorites ruetzleri*" *J. Organic Chemistry* 56(13):4304–4307.

Sanders, Scherer P. (1999) "Asthma, Viruses, and Nitric Oxide (44354)" *Proc. Soc. Exp. Biol. Med.* 220(3):123–132.

Scheuer, P.J., ed. (1978–1983) *Marine Natural Products, chemical and Biological Perspectives,* Academic Press, New York. (see entire book) copy not enclosed.

Sterling, R.G., S.A. Kharitonov, D. Campbell, D.S. Robinson, S.R. Durham, K.F. Chung, P.J. Barnes (1998) "Increase in exhaled nitric oxide levels in patients with difficult asthma and correlation with symptoms and disease severity despite treatment with oral and inhaled corticosteroids" *Thorax* 53(12):1030–1034.

Thorns, Veronika, Lawrence Hansen, Eliezer Masliah (1998) "nNOS Expressing Neurons in the Entorhinal Cortex and Hippocampus Are Affected in Patients with Alzheimer's Disease" *Experimental Neurology* 150:14–20.

Tsujii, Shinji, and L. Rinehart (1988) "Topsentin, Bromotopsentin, and Dihydrodexybromotopsentin: Antiviral and Antitumor Bis(indolyl)imidazoles from Caribbean Deep–Sea Sponges of the Family Halichondriidae. Structural and Synthetic Studies." *J. Org. Chem.* 53(23):5446–5453.

Uemura, Daisuke, Kanji Takahashi, Toshihiro Yamamoto et al. (1985) "Norhalichondrin A: An Antitumor Polyether Macrelide from a Marine Sponge" *J. Am. Chem. Soc.* 107:4796–4798.

Wright, Amy E., Shirley A. Pomponi, Sue S. Cross, Peter McCarthy (1992) "A New Bis(indole) Alkaloid from a Deep–Water Marine Spone of the Genus Spongosorites" *J. Org. Chem.* 57(17):4772–4775.

Yun, Hye–Young, Valina L. Dawson, Ted M. Dawson (1996) "Neurobiology of Nitric Oxide" *Critical Reviews in Neurobiology* 10(3/4):291–316.

USE OF IMIDAZOLE AND INDOLE COMPOUNDS AS INHIBITORS OF NITRIC OXIDE SYNTHASE

CROSS-REFERENCE TO A RELATED APPLICATION

This application claims priority from provisional application U.S. Ser. No. 60/093,283, filed Jul. 17, 1998.

BACKGROUND OF THE INVENTION

It has been found that some natural products and organisms are potential sources for chemical molecules having useful biological activity of great diversity. For example, marine sponges have proved to be such a source, and a number of publications have issued disclosing organic compounds derived from marine sponges. Such publications include Scheuer, P. J., Ed. [1978–1983] *Marine Natural Products, Chemical and Biological Perspectives*, Academic Press, New York; Faulkner, D. [1995] *J. Nat. Prod. Rep.* 12:223–269; [1994] 11:355–394; [1993] 10:497–539; [1992] 9:323–364; [1991] 8:97–147; [1990] 7:269–309; [1988] 5:613–663; [1987] 4:539–576; [1986] 3:1–33; [1984] 1:551–598; and Uemura, D., K. Takahashi, T. Yamamoto, C. Katayama, J. Tanaka, Y. Okumura, Y. Hirata [1985] *J. Am. Chem. Soc.* 107:4796–4798.

Indole compounds of marine origin have also been described in Moquin, C., M. Guyot [1984] *Tetrahedron Letters* 25(44):5047–5048 and Norton, R. S., R. J. Wells [1982] *J. Am. Chem. Soc.* 104(13):3628–3635.

Utilizing sponges as a source material and supplemented by novel synthetic production methods, new classes of biologically active compounds and new pharmaceutical compositions useful as, for example, antitumor and antiviral agents have been provided to the art. In a specific example, bis-heterocyclic compounds such as bis-indoles have been described as having antimicrobial, antitumor, or antiviral activity. Specifically, the bis-indole compounds known as topsentins are disclosed in U.S. Pat. No. 4,866,084. Dragmacidin and its related compounds isolated from the marine sponge of the Dragmacidon sp. are disclosed in U.S. Pat. No. 4,895,844. Similarly, the nortopsentins have been disclosed in U.S. Pat. No. 4,970,226. These patents are herein incorporated by reference. These compounds, as well as the homocarbonyltopsentins and hamacanthins, have also been described as having inhibitory activity against cellular inflammatory responses. See U.S. Pat. Nos. 5,290,777 and 5,464,835 which are also hereby incorporated by reference. Marine derived imidazole compounds have been described in the literature (Tsujii, S., K. L. Rinehart, S. P. Gunasekera, Y. Kashman, S. S. Cross, M. S. Lui, S. A. Pomponi, M. C. Diaz [19881] *J. Org. Chem.* 53:5446–5453; Sakemi, S. H. H. Sun [1991] *J. Org. Chem.* 56:4304–4307; Wright, A. E., S. A. Pomponi, S. S. Cross, P. McCarthy [1992] *J. Org. Chem.* 57:4772–4775). Marine derived indole compounds have also been described in the literature (Kohmoto, S., Y. Kashman, O. J. McConnell, K. L. Rinehart, A. E. Wright, F. Koehn [1988] *J. Org. Chem.* 53:3116–3118; Gunasekera, S. P., P. J. McCarthy, M. Kelly-Borges [1994] *J. Nat. Prod.* 10:1437–1441). The present invention provides a novel utility for these and related compounds, namely as inhibitors of neural nitric oxide production.

Since the discovery of its role in regulating vascular smooth muscle tone in the mid-1980's, the understanding of the physiologic and pathologic roles of nitric oxide (NO) has expanded significantly. The endogenous production of NO from the metabolism of L-arginine occurs by three well characterizednitric oxide synthase (NOS) enzymes: endothelial constitutive NOS (ecNOS), inducible NOS (iNOS) and brain or neural-derived NOS (bNOS or nNOS). This variety of NOS isoforms reflects the diverse range of activities attributed to NO. These activities include the regulation of blood pressure, gastric motility, anti-bacterial activity, and neurotransmission (Fukuto, J. M., G. Chaudhuri [1995] *Annu. Rev. Pharmacol. Toxicol.* 35:165–194; Yun, H. Y., V. L. Dawson, T. M. Dawson [1996] *Crit. Rev. Neurobiol.* 10:291–316; Molina, J. A., F. J. Jimenez-Jimenez, M. Orti-Pareja, J. A. Navarro [1998] *Drugs Aging* 12:251–259). The highly reactive and cytotoxic nature of NO is also suspected in several neurodegenerative disorders such as Alzheimer's, Parkinson's and Huntington's diseases (Molina, J. A., F. J. Jimenez-Jimenez, M. Orti-Pareja, J. A. Navarro [1998] *Drugs Aging* 12:251–259; Thorns, V., L. Hansen, E. Masliah [1998] *Exp. Neurol* 150:14–20). In addition, evidence from many lines of research indicate that brain inflammation contributes to the pathogenesis of Alzheimer's disease and that secretory products of activated glial cells, such as nitric oxide, mediate this inflammatory process (Gahtan, E. and J. B. Overmier [1999] *Neurosci: Biobehav. Rev.* 23:615–533; Hays, S. J. [1988] *Curr. Pharm. Ds.* 4(4):335–348; McCann, S. M. [1997] *Exp. Gerontol.* 32:431–440; McCann, S. M., J. Licinio, M. L. Wong, W. H. Yu, S. Karanth, and V. Rettorri [1998] *Exp. Gerontol.* 33(7–8):813–826. Inflammatory diseases, such as arthritis, owe their destructive properties to the over-production of nitric oxide by iNOS which is found in the synovial tissue and cartilage of affected arthritic joints (Amin, A. R., M. Attur, and S. B. Abramson [1999] *Curr. Opin. Rheumatol.* 11(3):202–209). Finally, evidence suggests the role of nitric oxide in the pathogenesis of asthma. High levels of exhaled nitric oxide are present in the exhalant of adult and pediatric patients, suggesting overproduction of nitric oxide as a consequence of the inflammatory process (Baraldi, E., C. Dario, R. Ongaro, M. Scollo, N. M. Azzolin, N. Panza, N. Paganini, and F. Zacchello [1999] *Am. J. Respir. Crit. Care Med.* 159(4 Pt. 1):1284–1288; Sanders, S. P. [1999] *Proc. Soc. Exp. Biol. Med.* 220(3):123–132; Stirling, R. G., S. A. Kharitonov, D. Campbell, D. S. Robinsin, S. R. Durham, K. F. Chung, P. J. Barnes [1998] *Thorax* 53(12):1030–1034). Therefore bNOS and iNOS are viable targets for the development of new therapeutic antagonists. Previous studies have shown that some imidazole unit containing compounds are able to inhibit bNOS (Fukuto, J. M., G. Chaudhuri [1995] *Annu. Rev. Pharmacol. Toxicol.* 35:165–194; Yun, H. Y., V. L. Dawson, T. M. Dawson [1996] *Crit. Rev. Neurobiol.* 10:291–316; Molina, J. A., F. J. Jimenez-Jimenez, M. Orti-Pareja, J. A. Navarro [1998] *Drugs Aging* 12:251–259; Thorns, V., L. Hansen, E. Masliah [1998] *Exp. Neutrol* 150:14–20; Handy, R. L. C., H. L. Harb, P. Wallace, Z. Gaffen, K. J. Whitehead, P. K. Moore [1996] *Brit. J. Pharmacol.* 119:423–431).

The advantages and scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns methods for blocking the production of nitric oxide (NO) by neural cells. Specifically, certain marine-derived imidazole and indole compounds were found to inhibit the activity of brain nitric oxide synthase (bNOS). The ability to inhibit bNOS is useful in therapeutic applications including the treatment of neurodegenerative diseases. Such diseases include, but are not limited to, Alzheimer's, Parkinson's and Huntington's diseases. In a further embodiment, certain compounds of the subject invention have been found to be useful in immune modulation including immune suppression and suppression of inflammatory reactions observed in neurodegenerative disorders, arthritis, and asthma.

The compounds whose activity in inhibiting NOS has been studied as described herein include topsentin, nortopsentin-C, hamacanthin-A, dragmacidin, and dragmacidin-D. The structures of these compounds are shown in FIG. 3. These compounds are disclosed in the following patents which are incorporated herein by reference: U.S. Pat. Nos. 4,866,084; 4,895,844; 4,970,226; 5,290,777; and 5,464,835.

In accordance with the subject invention it has been found that dragmacidin-D, hamacanthin-A, and dragmacidin are particularly preferred compounds for the inhibition of bNOS.

DETAILED DESCRIPTION OF THE INVENTION

Figure 1:
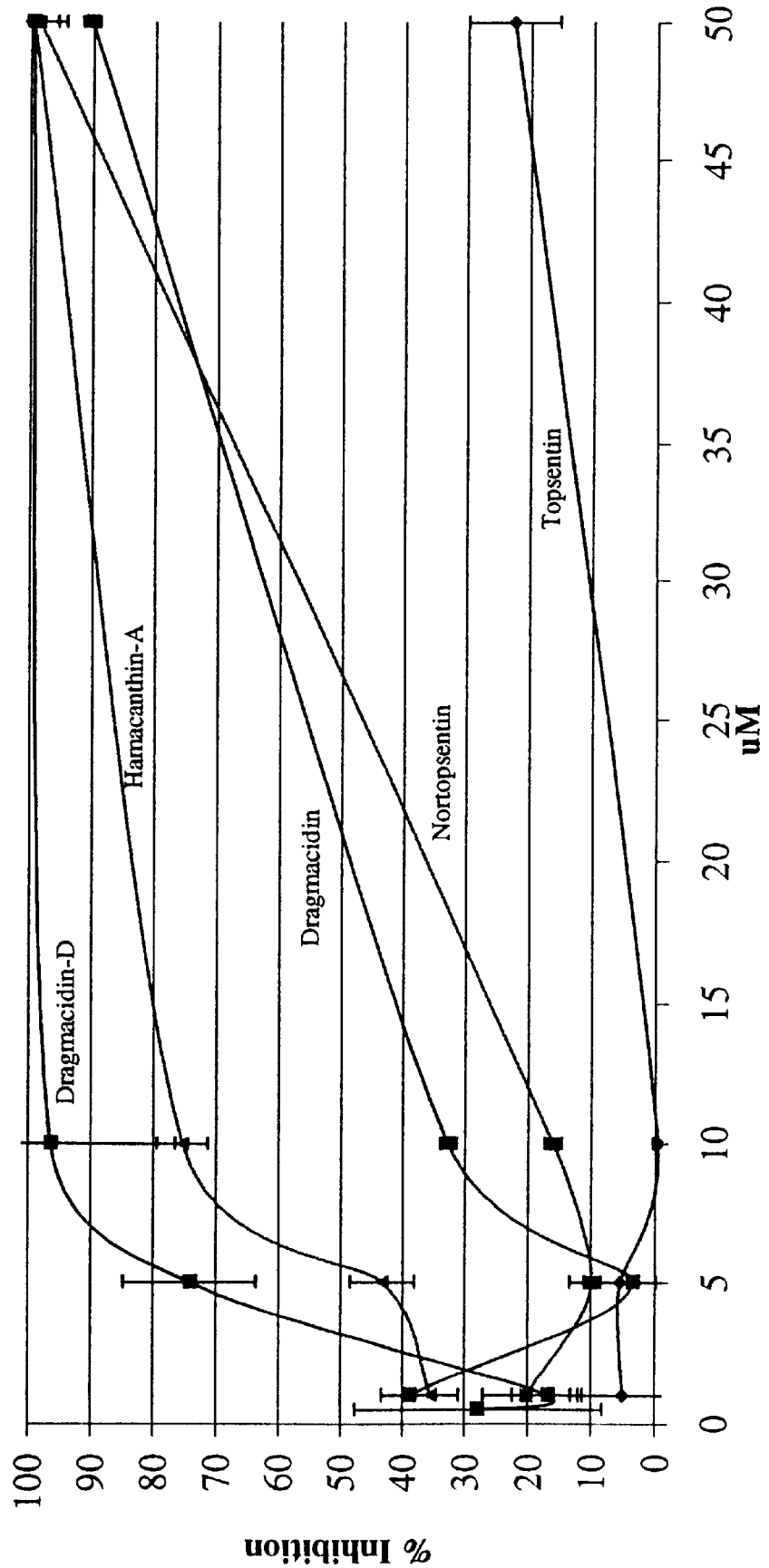
FIG. 1 shows inhibition of bNOS activity by marine-derived imidazole and indole compounds. Rat cerebral bNOS in working buffer was incubated with L-arginine and the nitrites produced after 15 minutes were measured using the Griess reaction. Results are presented as the % inhibition of bNOS activity as compared to a negative control (0% inhibition) and positive control (100% inhibition). Each point represents the average inhibition ± standard deviation of 4 wells.

The subject invention pertains to the use of imidizole and indole compounds for inhibiting the production of nitric oxide. In a preferred embodiment, the compounds of the subject invention inhibit the production of nitric oxide from neural cells. Specifically, these compounds have been shown to inhibit the activity of brain nitric oxide snythase (bNOS). In a particularly preferred embodiment, dragmacidin, dragmacidin-D, or hamacanthin-A can be used to inhibit nitric oxide production in neural cells.

The subject invention further pertains to use of the subject compounds as immunomodulators. In one embodiment, the subject invention pertains to the immunosuppressive use of the subject compounds. These compounds can be used to reduce, suppress, inhibit, or prevent unwanted immune responses. Advantageously, this immunosuppression can be achieved without cytotoxicity. Thus, the compounds of the subject invention are useful for treatments of humans or animals requiring immunosuppression. Examples of conditions for which immunosuppression is desired include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents.

In another embodiment, the compounds of the subject invention have been found to inhibit calcineurin. Calcineurin is an enzyme and a member of the serine/threonine phosphatase family of cell signal transduction proteins. Calcineurin is recognized to be a principal signaling molecule that regulates immune responsiveness. Calcineurin's phosphatase activity is inhibited through an association with a complex formed by the immunosuppressant FK506 and an intracellular protein, FKBP-12(FK506 Binding Protein), which results in immunosuppression. Therefore, inhibitors of calcineurin, such as the compounds of the subject invention, can be used to inhibit immune responsiveness through inhibition of calcineurin associated phosphatase activity. Inhibition of immune responsiveness by the subject compounds is useful for the treatment of conditions including systemic autoimmune disease, immunodeficiency diseases, immunotherapy of cancer or to prevent rejections of foreign organs or other tissues in transplants (i.e., kidney, heart, lungs, colon, liver, or bone marrow).

The compounds which are useful according to the subject invention can be readily obtained by those skilled in the art. Characteristics of these compounds, sources of the compounds, and methods of preparing the compounds (including derivatives and analogs) have been previously described. In this regard, U.S. Pat. Nos. 4,866,084; 4,895,844; 4,970,226; 5,290,777; and 5,464,835 are incorporated herein by reference.

The subject invention further pertains to pharmaceutical compositions which comprise the compounds as described herein. These pharmaceutical compositions would typically comprise a suitable pharmaceutical carrier in addition to the active ingredient(s).

In one set of experiments, the ability of marine-derived imidazole compounds (topsentin and nortopsentin-C and dragmacidin-D) and two related indole compounds (dragmacidin and hamacanthin-A) to inhibit the formation of nitrites by cerebral bNOS was examined. To further qualify these compounds as specific inhibitors of bNOS their activities against iNOS and calcineurin activities were measured as well as their cytotoxicity towards cultured murine macrophage RAW 264.7 cells. Calcineurin activity was used to indirectly assess the possibility that the bNOS inhibitory actions of the marine compounds acted via the inhibition of calmodulin a co-factor necessary for both bNOS (Bredt, D. S., S. H. Snyder [1990] *Proc. Natl. Acad. Sci. USA* 87:682–685) and calcineurin (Klee, C. B., H. Ren, X. Wang [1998] *J. Biol. Chem.* 273:13367–13370) activities.

Marine-derived imidazole and indole containing compounds were tested for their ability to inhibit rat cerebral NOS at a concentration range of 1.0 to 50 μM. The results are shown in Table 1.

TABLE 1

| bNOS | Topsentin | | Nortopsentin-C | | Hamacanthin-A | | Dragmacidin-D | | Dragmacidin | |
|---|---|---|---|---|---|---|---|---|---|---|
| Inhibition $\mu$M | % Inhib | Std Dev | % Inhib | Std Dev | % Inhib | Std Dev | % Inhib | Std Dev | % Inhib | Std Dev |
| 50 | 22.66 | 7.24 | 98.77 | 4.41 | 99.58 | 0.96 | 99.56 | 3.85 | 90.27 | 1.39 |
| 10 | −0.39 | 0.82 | 16.05 | 1.36 | 75.42 | 4.04 | 96.44 | 19.85 | 32.74 | 1.32 |
| 5 | 5.47 | 5.59 | 9.88 | 1.31 | 43.33 | 5.23 | 74.22 | 10.63 | 3.54 | 9.94 |
| 1 | 5.08 | 6.97 | 20.16 | 6.88 | 35.42 | 4.42 | 16.89 | 5.52 | 38.94 | 4.46 |

Topsentin had minimal inhibitory effects on the production of NO at these concentrations. Nortopsentin-C, hamacanthin-A, dragmacidin and dragmacidin-D inhibited bNOS activity with $IC_{50}$ values of approximately 27 $\mu$M, 7.5 $\mu$M, 20 $\mu$M and 4 $\mu$M, respectively (FIG. 1).

Activation of bNOS is dependent on the binding of calmodulin to the inactive NOS protein (Bredt, D. S., S. H. Snyder [1990] Proc. Natl. Acad. Sci. USA 87:682–685). Inhibition of calcineurin, a calmodulin-dependent enzyme (Klee, C. B., H. Ren, X. Wang [1998] J. Biol. Chem. 273:13367–13370), by marine-derived imidazoles and indoles was tested as an indirect means of assessing the effect of these compounds on calmodulin. Nortopsentin-C effectively inhibited calcineurin activity and had an $IC_{50}$ value of 11.4 $\mu$M, a concentration lower than its $IC_{50}$ for bNOS. This suggests that inhibition of calmodulin function by nortopsentin-C is a possible mechanism by which it inhibits bNOS activity. Although dragmacidin-D inhibited calcineurin activity ($IC_{50}$=10 $\mu$M) it was a more potent inhibitor of bNOS. Neither hamacanthin-A nor dragmacidin were able to inhibit calcineurin activity by more than 33% at concentrations below 50 $\mu$M.

Inhibition of whole cell iNOS activity by hamacanthin-A, dragmacidin and dragmacidin-D was tested to determine the specificity of the NOS inhibitory actions of these compounds. The results are shown in Table 2.

TABLE 2

| iNOS | Hamacanthin-A | | Dragmacidin-D | | Dragmacidin | |
|---|---|---|---|---|---|---|
| Inhibition $\mu$M | % Inhibit | Std Dev | % Inhibit | Std Dev | % Inhibit | Std Dev |
| 50 | 5.54 | 3.77 | 26.91 | 6.68 | 15.79 | 3.40 |
| 25 | 0.65 | 1.12 | 2.34 | 5.62 | 3.16 | 2.33 |
| 10 | 0.69 | 2.87 | −0.61 | 3.73 | −6.23 | 4.49 |
| 5 | −0.61 | 4.59 | −3.42 | 2.99 | −8.44 | 1.75 |
| 2.5 | 2.60 | 2.29 | −3.55 | 1.95 | −3.94 | 2.55 |

Figure 2:
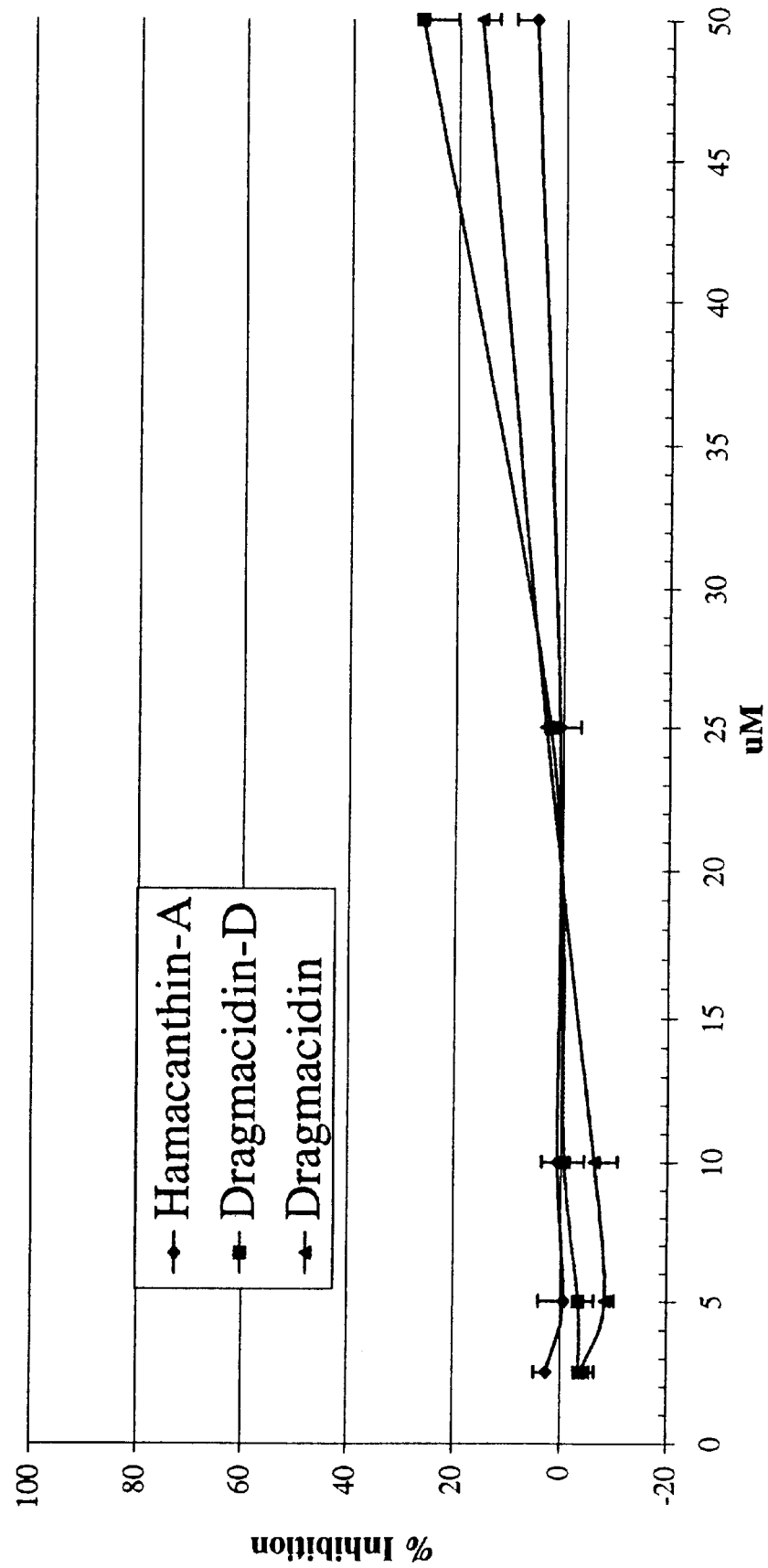
FIG. 2 shows inhibition of iNOS activity by hamacanthin-A, dragmacidin and dragmacidin-D. Murine macrophage RAW 264.7 cells were stimulated with lipopolysaccharide (LPS) and interferon-γ(IFN-γ) to induce iNOS production of nitric oxide co-incubated with test compounds for 24 hours. Resultant nitrites in the TCM were measured by the Griess reaction and compared to stimulated cells incubated in the absence of test compound (0% inhibition) and unstimulated cells (100% inhibition). Each point represents the average inhibition of 4 wells±standard deviation.
Figure 3:
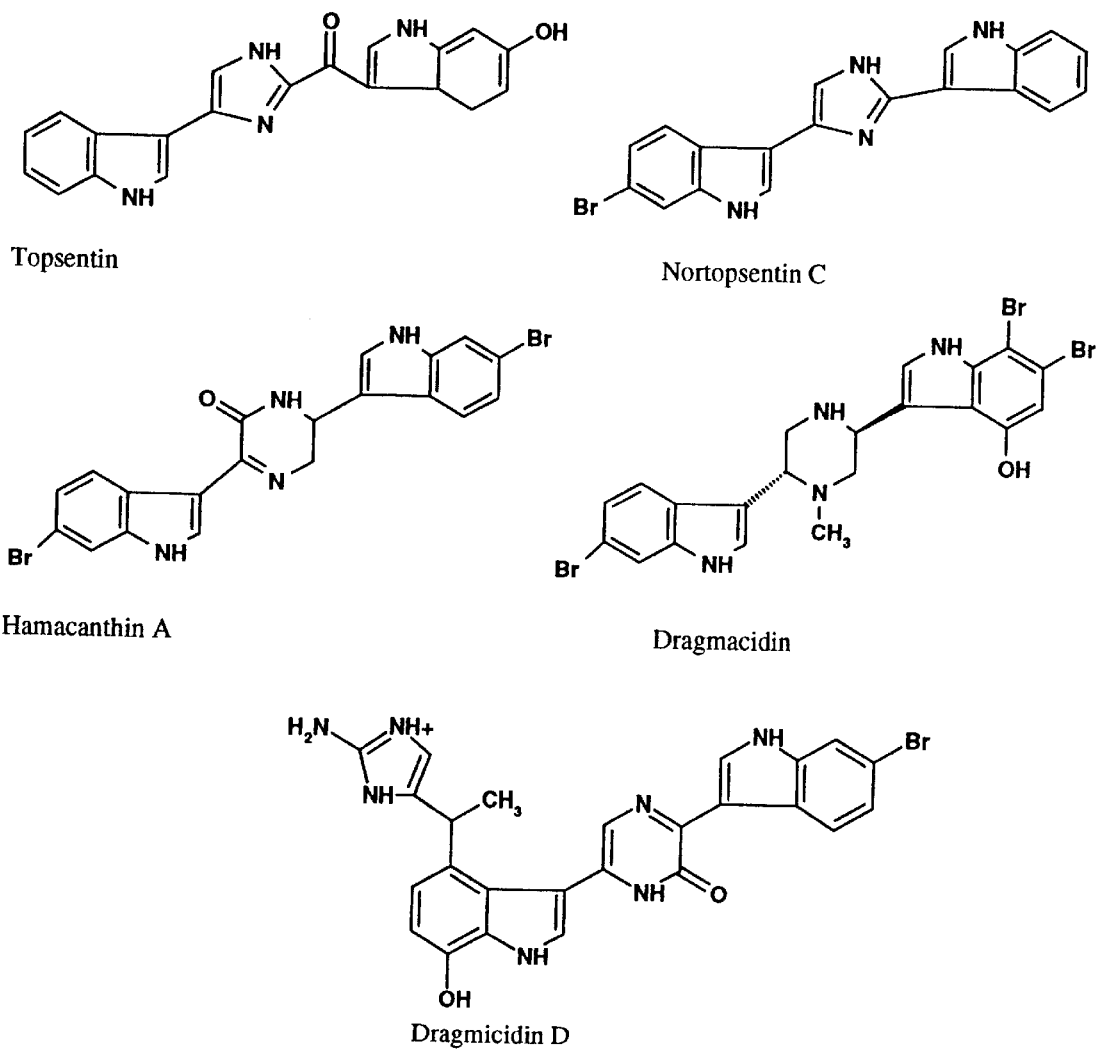
FIG. 3 shows structural formulae of the compounds tested.

None of these three compounds were able to inhibit the formation of nitrites by murine RAW 264.7 cells (FIG. 2) induced with interferon and lipopolysaccharide. Raw 264.7 cell viability, as measured by formation of formazan from MTT, was also not affected following 24 hours exposure to these compounds.

These results indicate that hamacanthin-A, dragmacidin and dragmacidin-D are able to specifically block the activity of bNOS. The ability to inhibit NO production by neural cells is useful in the treatment of neurodegenerative diseases. Topsentin and nortopsentin-C were not able to selectively inhibit rat cerebral bNOS at the concentrations tested and would, therefore, be less preferred as pharmaceutical compounds.

Following are examples which illustrate procedures for practicing the invention. These examples should not be construed as limiting. All percentages are by weight and all solvent mixture proportions are by volume unless otherwise noted.

EXAMPLE 1

Evaluation of bNOS Inhibition

Evaluation of activity of bNOS was performed by measuring nitrite production using the Griess reaction (Greenberg, S. S., J. Xie, J. J. Spitzer, J. F. Wang, J. Lancaster, M. B. Grisham, D. R. Powers, T. D. Giles [1995] Life Sci. 57:1949–1961) following an incubation of purified bNOS with L-arginine according to the methods of Ohshima et al. (Ohshima, H., S. Oguchi, H. Adachi, S. Iida, H. Suzuki, T. Sugimura, H. Esumi [1992] Biochem. Biophys. Res. Comm. 183:238–244). All reactions were carried out in 96 well microtiter plates. Briefly, imidazole and indole compounds were tested in reaction buffer (80 mM HEPES, pH 7.3; 1.0 mM EDTA; 1.5 mM $CaCl_2$) containing calmodulin (330 units/ml; Sigma Chemical Co.), dithiothreitol (1.3 mM), tetrahydrobiopterin (66 $\mu$M; Sigma), flavin adenine dinucleotide (16 $\mu$M; Sigma), and bovine brain nitric oxide synthase (1.67 units/ml; Sigma). The solutions were mixed and equilibrated at 37° C. for 2 minutes prior to the addition of L-arginine (113 $\mu$M; Sigma) and NADPH (200 $\mu$M; Sigma). Final reaction volume was 150 $\mu$l per well. The enzymatic reaction occurred at 37° C. for 15 minutes and nitrite formation detected by the addition of 100 $\mu$l of Greiss's reagent (1% sulfanilamide, 0.15% n-1-(naphthyl)-ethylenediamine dihydrochloride, 2.5% phosphoric acid; Sigma) and the color intensity determined by spectrophotometric absorbance at 540 nm (Spectra II; Tecan US Inc., Durham, N.C.).

EXAMPLE 2

Evaluation of Calcineurin Activity

Calcineurin activity was measured by the colorimetric method based on the dephosphorylation of p-nitrophenyl phosphate (PNPP) (Greenberg, S. S., J. Xie, J. J. Spitzer, J. F. Wang, J. Lancaster, M. B. Grisham, D. R. Powers, T. D. Giles [1995] Life Sci. 57:1949–1961) in a buffer of 0.5 mM $MnCl_2$, 1 mM dithiothreitol, 50 mM tris base (pH 7.5), 0.05 mM $CaCl_2$, and 10 $\mu$g/ml calmodulin (Sigma). Briefly, marine-derived compounds in ethanol were transferred to 96-well plates, air dried and resuspended in the working buffer. Calcineurin was added to a final concentration of 2.75 $\mu$g protein/ml and the enzyme allowed to equilibrate at 30° C. for 10 minutes prior to the addition of substrate. PNPP was added (final concentration≈50 mM) and the reaction mixture incubated at 30° C. for 1 hour. The optical density was measured at 405 nm in a Spectra II spectrophotometer.

EXAMPLE 3

Cell Cultures

RAW 264.7 cells were obtained from the American Type Culture Collection (Rockville, Md.) and maintained in tissue culture medium (TCM) (RPMI 1640 medium containing 100 U/ml penicillin, 100 μg/ml streptomycin, 60 μg/ml L-glutamine, 18 mM HEPES, 0.05 mg/ml gentamicin; Life Technologies, Gaithersburg, Md.) and supplemented with 10% rehatuin fetal bovine serum (Intergen Co., Purchase, N.Y.). Cells were subcultured at 3–4 day intervals, and used within 20 passages from the initial stock culture.

EXAMPLE 4

Evaluation of iNOS and MTT Activities

Test compounds were diluted in ethanol, aliquoted into appropriate wells of a 96 well microtiter plate and allowed to air dry for 1 hour at room temperature. RAW 264.7 cells were then subcultured into each well at a density of 5×10⁴ cells/well in 200 μl of TCM containing lipopolysaccharide (1 ng/ml; Sigma) and interferon-γ (2 units/ml; PharMingen, San Diego, Calif.). Plates were incubated at 37° C., 5% $CO_2$ for 24 hours. 150 μl of the TCM from each well was transferred to a second microtiter plate, 100 μl Griess reagent added to this TCM and the color intensity determined as above. Viability of the cells was determined by the methods of Mossman (Mossman, T. [1983] *J. Immunol. Methods* 65:55–63). Briefly, 150 μl of TCM containing 3-[4,5-dimethylthiazol-2-yl]-2,5-diphenyltetrazolium bromide (MTT, 2.5 mg/ml; Sigma) was added to each well containing the RAW 264.7 cells and incubated at 37° C., 5% $CO_2$ for 3 hours. The medium was removed from all wells and replaced with 200 μl of acidified isopropyl alcohol (0.2% HCl). The plates were shaken for 15 minutes and the presence of the blue formazan was detected using a Spectra II spectrophotometer set at 570 nm and with a 650 nm reference filter.

EXAMPLE 5

Formulation and Administration

The compounds of the invention are useful for various non-therapeutic and therapeutic purposes. It is apparent from the testing that the compounds of the invention are effective for inhibiting nitric oxide production.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration will be dependent upon the identity of the pathology to be treated, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's *Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the invention compounds, as a first active ingredient plus a second active ingredient known in the art.

In accordance with this invention, pharmaceutically effective amounts of a known therapeutic agent and the compounds of the subject invention are administered sequentially or concurrently to the patient. The most effective mode of administration and dosage regimen will depend upon the type of condition to be treated, the severity and course of that condition, previous therapy, the patient's health status and response, and the judgment of the treating physician. Pharmaceutical compositions may be administered to the patient at one time or over a series of treatments.

The compositions used in these therapies can also be in a variety of forms. These include, for example, solid, semi-solid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch, and equivalent carriers and diluents. While effective amounts may vary, as conditions in which compositions are used vary, a minimal dosage required for anti-inflammatory activity is generally between 0.01 and 100 μg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 50 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 50 mg/kg; and aerosol, 0.01 to about 50 mg/kg of animal (body) weight.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting nitric oxide synthase activity wherein said method comprises administering a nitric oxide synthase inhibiting amount of a compound selected from the group consisting of topsentin, nortopsentin-C, hamacanthin-A, dragmacidin-D, dragmacidin, and derivatives and analogs thereof.

2. The method, according to claim 1, wherein said compound is selected from the group consisting of nortopsentin-C, hamacanthin-A, dragmacidin-D, dragmacidin, and derivatives and analogs thereof.

3. A method for inhibiting the progression of a neurodegenerative process in an animal wherein said method comprises administering to said animal a neurodegeneration-inhibiting amount of a compound selected from the group consisting of topsentin, nortopsentin-C, hamacanthin-A, dragmacidin-D, dragmacidin, and derivatives and analogs thereof.

4. The method, according to claim 3, wherein said compound is selected from the group consisting of nortopsentin-C, hamacanthin-A, dragmacidin-D, dragmacidin, and derivatives and analogs thereof.

5. The method, according to claim 3, wherein said neurodegenerative process is selected from the group consisting of Alzheimer's, Parkinson's, and Huntington's diseases.

6. A method for inhibiting calcineurin activity wherein said method comprises administering a calcineurin-inhibiting amount of a compound selected from the group consisting of topsentin, nortopsentin-C, hamacanthin-A, dragmacidin-D, dragmacidin, and derivatives and analogs thereof.

7. The method, according to claim 6, wherein said compound is selected from the group consisting of nortopsentin-C, dragmacidin-D, and derivatives and analogs thereof.

* * * * *

UNITED STATES PATENT AND TRADEMARK OFFICE
CERTIFICATE OF CORRECTION

PATENT NO. : 6,087,363

DATED : July 11, 2000

INVENTOR(S) : Ross E. Longley, Richard A. Isbrucker, Amy E. Wright

It is certified that error appears in the above-identified patent and that said Letters Patent is hereby corrected as shown below:

Column 2, line 1: "characterizednitric" should read --characterized nitric--.

Column 2, line 51: "*Exp. Neutrol*" should read --*Exp. Neurol*--.

Column 7, line 4: "Md.)" should read --MD)--.

Column 7, line 15: "of 5 x 104" should read --of 5 x $10^4$--.

Signed and Sealed this

Seventeenth Day of April, 2001

Attest:

NICHOLAS P. GODICI

*Attesting Officer*   *Acting Director of the United States Patent and Trademark Office*